(12) United States Patent
Sasai et al.

(10) Patent No.: US 8,492,147 B2
(45) Date of Patent: Jul. 23, 2013

(54) METHOD OF INDUCING THE DIFFERENTIATION OF EMBRYONIC STEM CELLS INTO NERVE BY SERUM-FREE SUSPENSION CULTURE

(75) Inventors: Yoshiki Sasai, Kobe (JP); Kiichi Watanabe, Kobe (JP)

(73) Assignee: Riken, Wako-shi (JP)

( * ) Notice: Subject to any disclaimer, the term of this patent is extended or adjusted under 35 U.S.C. 154(b) by 336 days.

(21) Appl. No.: 11/570,579

(22) PCT Filed: Jun. 16, 2005

(86) PCT No.: PCT/JP2005/011476
§ 371 (c)(1),
(2), (4) Date: Jan. 22, 2007

(87) PCT Pub. No.: WO2005/123902
PCT Pub. Date: Dec. 29, 2005

(65) Prior Publication Data
US 2008/0044901 A1 Feb. 21, 2008

(30) Foreign Application Priority Data
Jun. 18, 2004 (JP) .................................. 2004-181770

(51) Int. Cl.
*C12N 5/00* (2006.01)
*C12N 5/02* (2006.01)

(52) U.S. Cl.
USPC .......................................... 435/377; 435/325

(58) Field of Classification Search
USPC .................................. 435/377, 325
See application file for complete search history.

(56) References Cited

U.S. PATENT DOCUMENTS

| | | | |
|---|---|---|---|
| 6,602,711 B1 * | 8/2003 | Thomson et al. | 435/378 |
| 2002/0151056 A1 | 10/2002 | Sasai et al. | |
| 2004/0224887 A1 * | 11/2004 | Jessel et al. | 514/12 |
| 2006/0281179 A1 | 12/2006 | Sasai et al. | |

FOREIGN PATENT DOCUMENTS

| | | |
|---|---|---|
| CA | 2298795 | 2/1999 |
| CA | 2315538 | 7/1999 |
| EP | 1 302 533 A1 | 4/2003 |
| JP | 2003-009854 A | 1/2003 |
| WO | WO 01/68815 A1 | 9/2001 |
| WO | WO 01/88100 A1 | 11/2001 |
| WO | WO 02/102369 A2 | 12/2002 |
| WO | WO 03/042384 A1 | 5/2003 |
| WO | WO 03/062405 A2 | 7/2003 |
| WO | WO 2004015077 A2 * | 2/2004 |

OTHER PUBLICATIONS

Lumelsky et al. 2001. Differentiation of Embryonic Stem Cells to Insulin-Secreting Structures Similar to Pancreatic Islets. Science. 292:1389-1394.*
Sato et al. Molecular signature of human embryonic stem cells and its comparison with the mouse Developmental Biology 260 (2003) 404-413.*
Rao. Conserved and divergent paths that regulate self-renewal in mouse and human embryonic stem cells. Developmental Biology 275 (2004) 269-286.*
Abeyta et al. Unique gene expression signatures of independently-derived human embryonic stem cell lines.Hum Mol Genet. Mar. 15, 2004;13(6):601-8.*
Schulz et al. Differentiation of Human Embryonic Stem Cells to Dopaminergic Neurons in Serum-Free Suspension Culture. Stem Cells 2004;22:1218-1238.*
Sasai. Generation of dopaminergic neurons from embryonic stem cells. J Neurol (2002) 249 [Supp 2]: II/41-II/44.*
Bain et al., *Developmental Biology*, 168: 342-357 (1995).
Finley et al., *The Journal of Neuroscience*, 16(3): 1056-1065 (Feb. 1, 1996).
Kawasaki et al., *Neuron*, 28: 31-40 (Oct. 2000).
Kawasaki et al., *Proc. Natl. Acad. Sci.*, 99(3): 1580-1585 (Feb. 5, 2002).
Lee et al., *Nature Biotechnology*, 18: 675-679 (Jun. 2000).
Mizuseki et al., *Proc. Natl. Acad. Sci.*, 100(10): 5828-5833 (May 13, 2003).
Ooto et al., *Investigative Ophthalmology & Visual Science*, 44(6): 2689-2693 (Jun. 2003).
Pera et al., *Genes & Dev.*, 17: 3023-3028 (2003).
Sasai et al., *Nature*, 376: 333-337 (Jul. 27, 1995).
Yamada et al., *Biochemical and Biophysical Research Communications*, 199(2): 552-563 (Mar. 15, 1994).
Ying et al., *Nature Biotechnology*, 21: 183-186 (Feb. 2003).
Branford et al., *Current Biology*, 12(24): 2136-2141 (Dec. 23, 2002).
Das et al., *Seminars in Ophthalmology*, 20(1): 3-10 (2005).
Gregory et al., *The Journal of Biology Chemistry*, 278(30): 28067-28078 (Jul. 25, 2003).
Ikeda et al., *PNAS*, 102(32): 11331-11336 (Aug. 9, 2005).
Kubo et al., *Development*, 131(7): 1651-1662 (2004).
Zhao et al., *Developmental Dynamics*, 229(2): 380-392 (2004).
Pankratz et al., Database Biosis [Online] Biosciences Information Service, Database Accession No. PREV200400203482 (2003) [Society for Neuroscience Abstract Viewer and Itinerary Planner, Abstract No. 673.5, 33rd Annual Meeting of the Society of Neuroscience, New Orleans, LA, Nov. 8-12, 2003].
Haruta et al., *Invest. Ophthalmol. Vis. Sci.*, 45(3): 1020-1025 (Mar. 2004).

(Continued)

*Primary Examiner* — Taeyoon Kim
(74) *Attorney, Agent, or Firm* — Leydig, Voit & Mayer, Ltd.

(57) ABSTRACT

The present invention provides a clinically applicable method of inducing differentiation of embryonic stem cells, particularly a method of inducing differentiation of embryonic stem cells into forebrain neurons. More specifically, the present invention provides a method of inducing differentiation of embryonic stem cells, comprising culturing the embryonic stem cells as a floating aggregate in a serum-free medium, particularly a method of inducing differentiation of the embryonic stem cells into nervous system cells such as forebrain neurons and cerebellar neurons and sensory organ cells; a floating aggregate of embryonic stem cells obtained by culturing the embryonic stem cells as a floating aggregate in a serum-free medium; and cells derived from a floating aggregate of embryonic stem cells, particularly nervous system cells such as forebrain neurons and cerebellar neuron, sensory organ cells such as retinal precursor cells, and the like.

18 Claims, No Drawings

OTHER PUBLICATIONS

Mizuseki et al., *Proc. Natl. Acad. Sci.*, 100(10): 5828-5833 (May 2003).
Watanabe et al., *Nature Neuroscience*, 8(3): 288-296 (Mar. 2005).
European Patent Office, Supplementary European Search Report in European Patent Application No. 05752560 (Jul. 8, 2008).
Hirami et al., *Neuroscience Letters*, 458: 126-131 (2009).
Japanese Patent Office, International Search Report in International Patent Application No. PCT/JP2005/011476 (Oct. 4, 2005).
Kim et al., *Stem Cell Rev. and Rep.*, 6: 270-281 (2010).
Osafune et al., *Nature Biotechnology*, 26(3): 313-315 with supplemental pp. 1-35 (2008).
Osakada et al., *Nature Biotechnology*, 26(2): 215-224 (2008).

* cited by examiner

METHOD OF INDUCING THE DIFFERENTIATION OF EMBRYONIC STEM CELLS INTO NERVE BY SERUM-FREE SUSPENSION CULTURE

TECHNICAL FIELD

The present invention relates to a method of inducing differentiation of embryonic stem cells, which comprises culturing embryonic stem cells as a floating aggregate in a serum-free medium, a cell culture obtained by the method and the like.

BACKGROUND ART

Embryonic stem cells are promising candidates for a source of cells for cell transplantation for Parkinson's disease and diabetes mellitus. However, even embryonic stem cells derived from mice, humans and other primates require the coexistence with mouse-derived feeder cells (stromal cells) in their culture and differentiation induction, and this represents a major barrier against their clinical applications.

Recently, the present inventors developed a method of inducing the differentiation of mouse and monkey embryonic stem cells into neurons at high efficiency (SDIA method) (see pamphlet for International Patent Publication No. WO01/088100; pamphlet for International Patent Publication No. WO03/042384; Kawasaki et al., Neuron, vol. 28, p. 31-40 (2000); Kawasaki et al., Proceedings of the National Academy of Sciences of the USA, vol. 99, p. 1580-1585 (2002); Mizuseki et al., Proceedings of the National Academy of Sciences of the United States of America, vol. 100, p. 5828-5833 (2003); Ooto et al., Invest. Opthalmol. Vis. Sci., vol. 44, p. 2689-2693 (2003)). Using this method, the present inventors succeeded in producing in vitro dopamine-secreting neurons, which are expected to be applied to transplantation therapy for Parkinson's disease, and motor neurons, which are speculated to be applied to treatment for amyotrophic lateral sclerosis, from mouse and monkey embryonic stem cells (see pamphlet for International Patent Publication No. WO01/088100; pamphlet for International Patent Publication No. WO03/042384; Kawasaki et al., Neuron, vol. 28, p. 31-40 (2000); Kawasaki et al., Proceedings of the National Academy of Sciences of the USA, vol. 99, p. 1580-1585 (2002); Mizuseki et al., Proceedings of the National Academy of Sciences of the United States of America, vol. 100, p. 5828-5833 (2003); Ooto et al., Invest. Opthalmol. Vis. Sci., vol. 44, p. 2689-2693 (2003)). Also, as another method of inducing the differentiation of neurons from embryonic stem cells, the multistep differentiation method is known (see Lee et al., Nature Biotech., vol. 18, p. 675-679 (2000)).

However, by the SDIA method and the multistep differentiation method, midbrain tissues such as dopamine nerves could be differentiation-induced efficiently, but forebrain tissues such as telencephalic tissue could only been induced at low efficiency.

Against this background, there has been a strong demand for the development of a method enabling the efficient induction of differentiation of embryonic stem cells into a forebrain tissue such as telencephalic tissue.

DISCLOSURE OF THE INVENTION

Accordingly, it is an object of the present invention to develop a highly practicable method that enables the induction of differentiation of embryonic stem cells, particularly into a forebrain tissue such as telencephalic tissue.

On the basis of the hypothesis concerning the reasons why forebrain tissues, particularly telencephalic tissue, could only be differentiation-induced at low efficiency by the SDIA method and the multistep differentiation method that 1) co-culture with feeder cells in the SDIA method, 2) addition of fibroblast growth factor (FGF) to the medium in the multistep method, and 3) treatment of embryoid body with serum and retinoic acid (RA) produce an environment wherein differentiation induction into the forebrain is difficult, the present inventors diligently investigated embryonic stem cell differentiation induction conditions in the absence of feeder cells, FGF, serum, and RA. As a result, the present inventors found that by culturing a floating aggregate of embryonic stem cells in a serum-free medium, nervous system cells can be differentiation-induced from ES cells at high efficiency, and that particularly under conditions in the absence of feeder cells, FGF, serum and/or RA, and by optimizing other various culture conditions, 85 to 95% of cells can be differentiation-induced into nervous system cells. The present inventors also succeeded at the same time in efficiently inducing the differentiation into not only forebrain tissues such as telencephalic tissue and cerebellar tissue, but also sensory organ cells, by cultivation under such conditions. Furthermore, according to this method, because it enables differentiation induction of embryonic stem cells without using an animal-derived cell as the induction-source, the risk of transplantation of cells obtained by culturing embryonic stem cells can be lessened to the risk level of allograft. Accordingly, the present invention is as follows:

(1) a method of inducing differentiation of embryonic stem cells, which comprises culturing the embryonic stem cells as a floating aggregate in a serum-free medium;
(2) the method (1) above, wherein the floating aggregate of the embryonic stem cells is cultured in the absence of feeder cells;
(3) the method (1) above, wherein the floating aggregate of the embryonic stem cells is cultured in the presence of a Nodal signal inhibitor or a Wnt signal inhibitor;
(4) the method (1) above, wherein the floating aggregate of the embryonic stem cells is cultured in the presence of a Nodal signal inhibitor and a Wnt signal inhibitor;
(5) the method (3) or (4) above, wherein the Nodal signal inhibitor is Lefty-A;
(6) the method (3) or (4) above, wherein the Wnt signal inhibitor is Dkk1;
(7) the method (1) above, wherein the serum-free medium is a medium substantially not comprising a Nodal signal promoter and/or a Wnt signal promoter;
(8) the method (1) or (2) above, wherein the serum-free medium is a medium substantially not comprising FGF;
(9) the method (1) or (2) above, wherein the serum-free medium is a medium substantially not comprising retinoic acid;
(10) the method (1) or (2) above, wherein the serum-free medium is a medium substantially not comprising BMP;
(11) the method (1) above, wherein the concentration of the embryonic stem cells at the start of cultivation is $1 \times 10^4$ to $5 \times 10^5$ cells/ml;
(12) the method (1) above, wherein cultivation of the embryonic stem cells is performed in a non-cell-adhesive culture vessel;
(13) the method (1) above, which comprises culturing the floating aggregate of the embryonic stem cells for at least 5 days;
(14) the method (1) above, which is a method of inducing differentiation of the embryonic stem cells into nervous system cells;

(15) the method (1) above, which further comprises culturing the obtained cells under adherent condition after cultivation of the floating aggregate of the embryonic stem cells;
(16) the method (1) or (15) above, which is a method of inducing differentiation of the embryonic stem cells into forebrain neurons;
(17) the method (1) or (15) above, which is a method of inducing differentiation of the embryonic stem cells into telencephalic neurons;
(18) the method (1) or (15) above, wherein the cells are cultured in the presence of an Shh signal promoter;
(19) the method (18) above, wherein the Shh signal promoter is Shh;
(20) the method (1) or (15) above, which is a method of promoting differentiation of the embryonic stem cells into ventral telencephalic neurons;
(21) the method (15) above, wherein culturing the obtained cells under adherent condition is performed in the presence of a Wnt signal promoter;
(22) the method (21) above, wherein the Wnt signal promoter is Wnt3a;
(23) the method (1) or (15) above, which is a method of promoting differentiation of the embryonic stem cells into dorsal telencephalic neurons;
(24) the method (1) above, wherein the cells are cultured in the presence of a Wnt signal promoter and/or a BMP signal promoter;
(25) the method (1) above, wherein the cells are cultured in the presence of a BMP signal promoter and/or FGF;
(26) the method (1), (24) or (25) above, which is a method of inducing differentiation of the embryonic stem cells into cerebellar neurons;
(27) the method (1), (24) or (25) above, which is a method of inducing differentiation of the embryonic stem cells into cerebellar granule cells or cerebellar Purkinje's cells;
(28) the method (1) above, which comprises adding serum during cultivation of the floating aggregate of the embryonic stem cells in the serum-free medium;
(29) the method (28) above, wherein the cells are cultured in the presence of an Shh signal promoter;
(30) the method (28) or (29) above, wherein the cells are cultured in the presence of an Nodal signal promoter;
(31) the method (28) or (29) above, wherein the cells are cultured in the presence of a Wnt signal inhibitor and/or a Nodal signal inhibitor;
(32) the method (28) above, wherein the cells are cultured in the presence of Lefty-A, Dkk1 and activin;
(33) the method (28) above, which is a method of inducing differentiation of the embryonic stem cells into sensory organ cells;
(34) the method (32) above, which is a method of inducing differentiation of the embryonic stem cells into retinal system cells;
(35) a floating aggregate of the embryonic stem cells, which is obtained by culturing the embryonic stem cells as a floating aggregate in a serum-free medium;
(36) a cell culture which can be obtained by any of the methods (1) to (34) above;
(37) a cerebellar neuron which is differentiation-induced from ES cell;
(38) the cell (37) above, which is a cerebellar granule cell;
(39) the cell (37) above, which is a cerebellar Purkinje's cell;
(40) a retinal system cell having the capability of differentiating into visual cell, wherein the retinal system cell is differentiation-induced from ES cell.

The present invention is useful from the viewpoint of the application to cell therapy for neurodegenerative disease, sensory organ disease and the like because it enables the efficient induction of differentiation of embryonic stem cells into nervous system cells and sensory organ cells. The present invention is particularly useful from the viewpoint of the application to cell therapy for diseases characterized by abnormalities in tissues such as forebrain tissue, cerebellar tissue, and retinal tissue because it enables the efficient induction of differentiation of embryonic stem cells into forebrain tissues (particularly telencephalic tissue), which has been difficult by conventional differentiation methods, and also because it enables the induction of differentiation of embryonic stem cells into cerebellar tissue, which has never been achieved successfully, and enables the induction of differentiation of embryonic stem cells into retinal tissue, which can be efficiently differentiated into optic nerves. The present invention is further useful because it enables the induction of differentiation of embryonic stem cells without using an animal-derived cell as the induction source, and also because the risk of transplantation of cells obtained by culturing embryonic stem cells can be lessened to the risk level of allograft.

BEST MODE FOR EMBODYING THE INVENTION

The present invention provides a method of inducing differentiation of embryonic stem cells, which comprises culturing the embryonic stem cells as a floating aggregate in a serum-free medium. The present invention is hereinafter described in detail.

(1. Embryonic Stem Cell)

The embryonic stem cell refers to a cell which can be cultured in vitro and have a pluripotency capable of differentiating into all cells constituting the living body.

As the embryonic stem cell, a cell derived from, for example, a warm blood animal, preferably, a mammal, can be used. The mammal includes, for example, mouse, rat, guinea pig, hamster, rabbit, cat, dog, sheep, pig, cattle, goat, monkey and human.

Specifically, examples of the embryonic stem cell include an embryonic stem cell of a mammal and the like established by culturing an early embryo before implantation (hereinafter, abbreviated as "embryonic stem cell I"), an embryonic stem cell established by culturing an early embryo produced by nuclear transplantation of the nucleus from a somatic cell (hereinafter abbreviated as "embryonic stem cell II"), and an embryonic stem cell in which a gene on the chromosome of the embryonic stem cell of the embryonic stem cell I or II is modified using a gene engineering technique (hereinafter abbreviated as "embryonic stem cell III").

More specifically, the embryonic stem cell I includes an embryonic stem cell established from an early embryo-constituting inner cell mass, an EG cell established from a primordial germ cell, a cell isolated from a cell population (e.g., primitive ectoderm) having a pluripotency of an early embryo before implantation, and a cell obtained by culturing such a cell.

The embryonic stem cell I can be prepared by culturing an early stage embryo before implantation according to the method described in a reference (Manipulating the Mouse Embryo A Laboratory Manual, Second Edition, Cold Spring Harbor Laboratory Press (1994)).

The embryonic stem cell II can be prepared as described below, for example, by using a method reported by, e.g., Wilmut et al. (Nature, 385, 810 (1997)), Cibelli et al. (Science, 280, 1256 (1998)), Akira Iritani et al. (Protein, Nucleic Acid and Enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)) or Rideout III et al (Nature Genetics, 24, 109 (2000)).

An egg which acquired the nucleus of other somatic cell and started normal development can be obtained by starting its development using a method in which the nucleus of a mammal cell is excised, initialized (an operation to return the nucleus to such a state that it can repeat the development again) and injected into an enucleated unfertilized egg of a mammal, and then incubating the development-started egg.

As the method for initializing the nucleus of a somatic cell, several methods are known. For example, the initialization can be carried out by changing the medium for culturing a nuclear donor cell from a medium containing from 5 to 30%, preferably 10%, of fetal calf serum (e.g., M2 medium) to a poor nutrient medium containing from 0 to 1%, preferably 0.5%, of fetal calf serum and culturing the cell for a period of from 3 to 10 days, preferably 5 days, thereby to induce the cell cycle into an interphase state (G0 phase or G1 phase).

Also, the initialization can be carried out by injecting the nucleus of a nucleus donor cell into an enucleated unfertilized egg from a mammal of the same species and incubating the egg for several hours, preferably from about 1 to 6 hours.

The thus initialized nucleus becomes possible to start its development in an enucleated unfertilized egg. Several methods are known as the method for starting development of the initialized nucleus in an enucleated unfertilized egg. The development can be started by transplanting a nucleus initialized by inducing the cell cycle into an interphase state (G0 phase or G1 phase) into an enucleated unfertilized egg from a mammal of the same species, e.g., by electrofusion method to thereby activate the egg.

Development of the nucleus initialized by injecting it into an enucleated unfertilized egg from a mammal of the same species can be carried out by again transplanting it into an enucleated unfertilized egg from a mammal of the same species, for example, using a method which uses a micromanipulator, stimulating it with an egg activating factor (e.g., strontium) and then treating it with a cell division inhibitor (e.g., cytochalasin B) to suppress release of a secondary polar body. This method is suitable, for example, when the mammal is a mouse or the like.

Once an egg which started the development is obtained, the embryonic stem cell can be obtained by a known method described in, for example, Manipulating the Mouse Embryo A Laboratory Manual, Second Edition, Cold Spring Harbor Laboratory Press (1994); Gene Targeting, A Practical Approach, IRL Press at Oxford University Press (1993); Biomanual series 8 Gene Targeting, Preparation of mutant mouse using ES cell, Yodosha (1995) and the like.

The embryonic stem cell III can be prepared, for example, using homologous recombination techniques. Examples of the chromosomal gene to be modified for producing the embryonic stem cell III include genes for histocompatibility antigens and genes related to diseases based on disorders of nervous system cells. Modification of the target gene on the chromosome can be carried out using a method described in, for example, Manipulating the Mouse Embryo A Laboratory Manual, Second Edition, Cold Spring Harbor Laboratory Press (1994); Gene Targeting, A Practical Approach, IRL Press at Oxford University Press (1993); Biomanual series 8 Gene Targeting, Preparation of mutant mouse using ES cell, Yodosha (1995) and the like.

Specifically, a genomic gene of the target gene to be modified (e.g., a histocompatibility antigen gene or a disease-related gene) is isolated, and a target vector for homologous recombination of the target gene is produced using the isolated genomic gene. An embryonic stem cell having a modified chromosomal gene can be produced by introducing the thus produced target vector into embryonic stem cells and selecting a cell in which homologous recombination occurred between the target gene and the target vector.

The method for isolating genomic gene of the target gene include a known method described in Molecular Cloning, A Laboratory Manual, Second Edition, Cold Spring Harbor Laboratory Press (1989), Current Protocols in Molecular Biology, John Wiley & Sons (1987-1997) and the like. The genomic gene of the target gene can also be isolated, for example, using Genome DNA Library Screening System (manufactured by Genome Systems) or Universal GenomeWalker™ Kits (manufactured by CLONTECH).

The preparation of target vector for carrying out homologous recombination of the target gene and efficient selection of a homologous recombinant can be performed according to the method described in, for example, Gene Targeting, A Practical Approach, IRL Press at Oxford University Press (1993); Biomanual series 8 Gene Targeting, Preparation of mutant mouse using ES cell, Yodosha (1995) and the like. As the target vector, any one of its replacement type and insertion type can be used. As the selection method, the positive selection, promoter selection, negative selection, poly A selection or the like can be used.

The method for selecting the homologous recombinant of interest from the selected cell lines includes the Southern hybridization, PCR and the like for genomic DNA.

Furthermore, the embryonic stem cell is obtained from certain institution and a commercial product thereof can also be purchased. For example, human embryonic stem cells, KhES-1, KhES-2 and KhES-3 are available from Institute for Frontier Medical Sciences, Kyoto University.

Embryonic stem cells can be maintain-cultured by a method known per se. For example, embryonic stem cells can be maintained by cultivation in the absence of feeder cells with the addition of fetal calf serum (FCS), Knockout™ Serum Replacement (KSR), and LIF.

(2. Cells that can be Differentiation-Induced from Embryonic Stem Cells by the Method of the Present Invention)

By the method of the present invention, differentiated cells of embryonic stem cells can be obtained. Although the differentiated cells of embryonic stem cells may be any of endodermal cells, mesodermal cells, and ectodermal cells, they are preferably ectodermal cells. As examples of the ectodermal cells, nervous system cells, epidermal system cell, sensory organ cells, pigment cells, and neural crest-derived mesenchymal cells can be mentioned.

The identity of the cells obtained by the method of the present invention can be confirmed by a method known per se, for example, the expression of a cell marker. For example, whether or not the cells obtained by the method of the present invention are endodermal cells or mesodermal cells can be confirmed by the expression of an endodermal cell marker (for example, Sox17, AFP) or a mesodermal cell marker (for example, Brachyury, Flk1, Mox).

Whether or not the cells obtained by the method of the present invention are ectodermal cells can be confirmed by, for example, the expression of a nervous system cell marker. As examples of the nervous system cell marker, NCAM, TuJ1, tyrosine hydroxylase (TH), serotonin, nestin, MAP2, MAP2ab, NeuN, GABA, glutamates, ChAT, and Sox1 can be mentioned.

Also, whether or not the cells obtained by the method of the present invention are ectodermal cells can also be confirmed by the expression of an epidermal system cell marker (for example, cytokeratin), a sensory organ cell marker (for example, RPE, rhodopsin), a pigment cell marker (for example, TRP-1), or a neural crest-derived mesenchymal cell marker (for example, SMA)

Described in detail below are nervous system cells and sensory organ cells as examples of ectodermal cells that can be differentiation-induced by the method of the present invention.

(2.1. Nervous System Cells)

The nervous system cell which can be differentiation-induced by the method of the present invention includes, for example, neural stem cell, neuron, cell of neural tube, cell of neural crest and the like.

The neural stem cell refers to a cell having an ability to be capable of differentiating into a neuron, an astrocyte and an oligodendrocyte and having self-replicating ability, and it functions to supply a neuron, an astrocyte and an oligodendrocyte in the brain. Accordingly, methods of confirming that the cell is the neural stem cell include a method in which the cell is actually transplanted into the brain and its differentiation ability is confirmed and a method in which inducing differentiation of the neural stem cell into a neuron, an astrocyte and an oligodendrocyte is confirmed in vitro (Mol. Cell. Neuro Science, 8, 389 (1997); Science, 283, 534 (1999)). Also, the neural stem cell having such a function can be stained with an anti-nestin antibody which recognizes a cytoskeletal protein nestin whose expression in a nerve precursor cell has been confirmed (Science, 276, 66 (1997)). Accordingly, the neural stem cell can be confirmed by staining with the anti-nestin antibody.

The neuron refers to a cell which functions to receive a stimulus from other neurons or stimulus receptor cells and transmit the stimulus to another neurons, muscle or glandular cells.

The neuron is classified based on the difference in the neurotransmitter produced by the neurons, for example, based on the difference in the secreted neurotransmitter and the like. Examples of neurons classified by these neurotransmitters include dopamine-secreting neurons, acetylcholine-secreting neurons, serotonin-secreting neurons, noradrenaline-secreting neurons, adrenaline-secreting neurons, glutamate-secreting neurons and the like. The dopamine-secreting neurons, the noradrenaline-secreting neurons and the adrenaline-secreting neurons are generally referred to as catecholamine-secreting neurons.

Alternatively, the nervous system cells such as nervous stem cells and neurons obtained by the method of the present invention can be characterized by cell markers. The nervous system cells obtained by the method of the present invention are positive for Sox1 at a high frequency, for example, at a frequency of about 80% or more, preferably about 80 to 90%. Also, the nervous system cells obtained by the method of the present invention are characterized by being positive for the forebrain neuron markers and cerebellar neuron markers described below.

From another viewpoint, neurons can be classified according to the difference in the site where the neurons exist. As examples of the these neurons classified according to the difference in the site where they exist, forebrain neurons, midbrain neurons, cerebellar neurons, metencephalic neurons, spinal neurons and the like can be mentioned. The method of the present invention enables the induction of differentiation of embryonic stem cells into these optionally chosen cells, and particularly enables the efficient induction of differentiation of embryonic stem cells into forebrain neurons and cerebellar neurons. Described in detail below are forebrain neurons and cerebellar neurons.

(2.1.1. Forebrain Neurons)

According to the method of the present invention, as neurons, forebrain neurons, particularly telencephalic neurons, can be differentiation-induced more efficiently. The forebrain neuron refers to a neuron present in forebrain tissue (that is, the tissue composed of the telencephalon and the diencephalon) or a precursor cell destined to differentiate into a neuron present in forebrain tissue. Forebrain neurons can be classified into telencephalic neurons and diencephalic neurons (for example, thalamic cells, and hypothalamic cells). Telencephalic neurons can be further classified into dorsal cells (for example, cerebrocortical cells) and ventral cells (for example, cerebral basal ganglia cells).

Whether or not the cells obtained by the method of the present invention are forebrain neurons can be confirmed by a method known per se, for example, the expression of a forebrain neuron marker. As the forebrain neuron marker, Otx1 (forebrain), Bf1 (telencephalon), Emx1 (dorsal telencephalon), Gsh2 and Nkx2.1 (ventral telencephalon) and the like can be mentioned.

According to the method of the present invention, it is possible to efficiently induce the differentiation of embryonic stem cells into telencephalic neurons out of forebrain neurons.

In one aspect, the method of the present invention can efficiently induce differentiation of embryonic stem cell into ventral telencephalic neurons out of telencephalic neurons, and conversely can efficiently suppress differentiation of embryonic stem cell into ventral forebrain neurons. The ventral telencephalic neuron refers to a neuron present in ventral telencephalic tissue, or a precursor cell destined to differentiate into a neuron present in ventral telencephalic tissue. As examples of the ventral telencephalic tissue, the cerebral basal ganglia can be mentioned.

Whether or not the cells obtained by the method of the present invention are ventral telencephalic neurons can be confirmed by a method known per se, for example, the expression of a ventral telencephalic neuron marker. As examples of the ventral telencephalic neuron marker, cerebral basal ganglia neuron markers (for example, Gsh2, Mash1) and hypothalamic neuron markers (for example, NRx2.1, NRx2.2) can be mentioned.

In another aspect, the method of the present invention can efficiently induce of differentiation of embryonic stem cells into dorsal telencephalic neurons out of telencephalic neurons, and conversely can efficiently suppress differentiation of embryonic stem cells into dorsal forebrain neurons. The dorsal telencephalic neuron refers to a neuron present in dorsal telencephalic tissue, or a precursor cell destined to differentiate into a neuron present in dorsal telencephalic tissue. As examples of the dorsal telencephalic tissue, cerebral cortex can be mentioned.

Whether or not the cells obtained by the method of the present invention are dorsal telencephalic neurons can be confirmed by a method known per se, for example, the expression of a dorsal telencephalic neuron marker. As examples of the dorsal telencephalic neuron marker, cerebrocortical neuron markers (for example, Pax6, Emx1) can be mentioned.

Alternatively, from another viewpoint, the forebrain neurons (particularly telencephalic neurons) obtained by the method of the present invention can be characterized by cell markers. The forebrain neurons obtained by the method of the present invention are positive for Bf1 at a high frequency, for example, at a frequency of about 10% or more, preferably about 10 to 50%, more preferably about 10% to 30%. By the conventional SDIA method, Bf1+ cells could only been differentiation-induced from embryonic stem cells at a frequency of about 1%, but the method of the present invention has made it possible to obtain Bf1+ cells at a high frequency.

Of the Bf1+ cells obtained by the method of the present invention, for example, about 20% or more, preferably about 20 to 80%, more preferably about 20 to 50%, can be positive for Gsh. Also, of the Bf1+ cells obtained by the method of the present invention, for example, about 5% or more, preferably about 5 to 50%, more preferably about 5 to 20%, can be positive for NRx2.1. Furthermore, of the Bf1+ cells obtained by the method of the present invention, for example, about 10% or more, preferably about 10 to 90%, more preferably about 10 to 50%, can be positive for Pax. Also, of the Bf1+ cells obtained by the method of the present invention, for example, about 5% or more, preferably about 5 to 50%, more preferably about 5 to 20%, most preferably about 10 to 20%, can be positive for Emx1.

(2.1.2. Cerebellar Neurons)

According to the method of the present invention, as neurons, cerebellar neurons can be differentiation-induced efficiently. The cerebellar neuron refers to a neuron present in cerebellar tissue, or a precursor cell destined to differentiate into a neuron present in cerebellar tissue. As examples of the cerebellar neuron, cerebellar granule cells, Purkinje's cells, and precursor cells of these cells can be mentioned. Although none has been reported to succeed in differentiation-inducing cerebellar neurons, the method of the present invention has made it possible to obtain cerebellar neurons.

Whether or not the cells obtained by the method of the present invention are cerebellar neurons can be confirmed by a method known per se, for example, the expression of a cerebellar neuron marker. As examples of the cerebellar neuron marker, cerebellar granule cell markers (for example, Math1, Pax6, Zic1) and Purkinje's cell markers (for example, L7) can be mentioned.

Also, whether or not the cells obtained by the method of the present invention are cerebellar neurons can be confirmed by their phenotype. For example, whether or not the cells obtained are cerebellar granule cells can be confirmed by recognizing that they are able to migrate in adhesion to parallel fiber axons, and/or that T-shaped axons have elongated.

Alternatively, the cerebellar neurons obtained by the method of the present invention can be characterized by cell markers. The cerebellar neurons obtained by the method of the present invention are positive for Math1 at a high frequency, for example, at a frequency of 30% or more, preferably about 30 to 60%, more preferably about 40% to 50%.

Of the Math1+ cells obtained by the method of the present invention, for example, about 40% or more, preferably about 40 to 60%, more preferably about 50%, can be positive for Pax6 and/or Zic1. Also, of the Math1+ cells obtained by the method of the present invention, for example, about 40% or more, preferably about 40 to 80%, more preferably about 50 to 60%, can be positive for Ki67.

(2.2. Sensory Organ Cells)

According to the method of the present invention, sensory organ cells can be differentiation-induced from embryonic stem cells efficiently. The sensory organ cell refers to a neuron present in a sensory organ, or a precursor cell destined to differentiate into a neuron present in a sensory organ. As the sensory organ cells obtained by the method of the present invention, retinal cells, olfactory epithelial cells, and inner ear hair cells can be mentioned.

Whether or not the cells obtained by the method of the present invention are sensory organ cells can be confirmed by a method known per se, for example, the expression of a sensory organ cell marker. As examples of the sensory organ cell marker, Rx (retinal precursor cells), Crx (visual cells), and rhodopsin (visual cells) can be mentioned.

According to the method of the present invention, sensory organ cells, particularly retinal system cells (that is, retinal cells or precursor cells thereof), can be differentiation-induced efficiently.

Alternatively, the sensory organ cells obtained by the method of the present invention can be characterized by cell markers. The sensory organ cells obtained by the method of the present invention are positive for Rx at a high frequency, for example, at a frequency of 5% or more, preferably about 5 to 20%, more preferably about 10% to 15%.

Of the Rx+ cells obtained by the method of the present invention, for example, about 1% or more, preferably about 1 to 10%, more preferably about 1 to 5%, can be positive for Crx and/or rhodopsin.

The retinal system cells obtained by the method of the present invention efficiently differentiate into visual cells by tissue culture with retinal tissue, and they can exhibit a rhodopsin positivity rate of, for example, about 10% or more, preferably about 10% to 30% (e.g., about 20%). The retinal system cells obtained by the method of the present invention also have the capability of entering the visual cell layer; about 30% or more, for example, about 30% to 50% (e.g., about 40%), of the cells entering visual cells can be positive for rhodopsin, and are further capable of exhibiting visual cell-specific morphologies such as outer segment structure.

(3. Method of Culturing a Floating Aggregate of Embryonic Stem Cells in Serum-Free Medium)

"Culturing embryonic stem cells as a floating aggregate" refers to culturing a group of embryonic stem cells that have assembled to form a clamp in a culture medium under conditions that are non-adhesive to the cell culture vessel. This type of cultivation is hereinafter abbreviated as floating culture as required.

When embryonic stem cells are subjected to floating culture, it is preferable to perform the culture in the absence of feeder cells in order to make the formation of a floating aggregate more easily, and/or for the efficient induction of differentiation (for example, differentiation induction into ectodermal cells such as nervous system cells and sensory organ cells).

The medium used in the floating culture can be prepared using a medium used for culturing an animal cell as a basal medium. The basal medium is not limited as long as it is available for culturing an animal cell, and include, for example, BME medium, BGJb medium, CMRL 1066 medium, Glasgow MEM medium, Improved MEM Zinc Option medium, IMDM medium, Medium 199 medium, Eagle's MEM medium, αMEM medium, DMEM medium, Ham's medium, RPMI 1640 medium, Fischer's medium and a mixed medium thereof and the like.

When the embryonic stem cell is floating-cultured, a serum-free medium is used as a medium. Here, a serum-free medium means a medium not containing an unadjusted or unpurified serum, and a medium supplemented with a purified blood-derived component or animal tissue-derived component (e.g., growth factor) is deemed a serum-free medium.

The serum-free medium used in the floating culture can be, for example, one containing a serum replacement. The serum replacement can be, for example, one containing as appropriate albumins (for example, lipid-rich albumins), transferrin, fatty acids, insulin, collagen precursor, trace elements, 2-mercaptoethanol or 3'-thiolglycerol, or equivalents thereof and the like. This serum replacement can be prepared by, for example, a method described in WO98/30679. Also, to perform the method of the present invention more conveniently, a commercially available serum replacement can be utilized. As examples of the commercially available serum replacement, knockout Serum Replacement (KSR), Chemically-defined Lipid concentrated (manufactured by Gibco Company), and Glutamax (manufactured by Gibco Company) can be mentioned.

Also, the serum-free medium used in the method of the present invention can contain fatty acids or lipids, amino acids (for example, non-essential amino acids), vitamins, growth factors, cytokines, antioxidants, 2-mercaptoethanol, pyruvic acid, buffering agents, inorganic salts and the like. For example, the 2-mercaptoethanol is not subject to limitation, as long as it is used at a concentration suitable for the cultivation of embryonic stem cells, and it can be used at a concentration of, for example, about 0.05 to 1.0 mM, preferably about 0.1 to 0.5 mM, more preferably about 0.2 mM.

The serum-free medium used in the floating culture is not subject to limitation, as long as it is as described above. However, from the viewpoint of avoiding the painstaking work for preparation, a serum-free medium (GMEM or dMEM, 0.1 mM 2-mercaptoethanol, 0.1 mM non-essential amino acid Mix, 1 mM sodium pyruvate) supplemented with an appropriate amount (for example, 1-20%) of commercially available KSR as the serum-free medium can be used.

The culture vessel used for floating-culture is not limited as long as it is capable of floating-culturing cells, and include, for example, a flask, a tissue culture flask, a dish, a Petri dish, a tissue culture dish, a multi-dish, a microplate, a micro-well plate, a multi-plate, a multi-well plate, a chamber slide, a schale, a tube, a tray, a culture bag, a roller bottle and the like.

When embryonic stem cells are subjected to floating culture, the culture vessel is preferably non-cell-adhesive. As a non-cell-adhesive culture vessel, a culture vessel whose surface has not been artificially treated (for example, coating treatment with extracellular matrix and the like) to improve their adhesion with cells can be used.

The concentration of embryonic stem cells at the start of cultivation can be set as appropriate to allow the more efficient formation of a floating aggregate of embryonic stem cells. The concentration of embryonic stem cells at the start of cultivation is not subject to limitation, as long as it is a concentration enabling the formation of a floating aggregate of embryonic stem cells; it can be, for example, about $1\times10^4$ to about $5\times10^5$ cells/ml, preferably about $3\times10^4$ to about $1\times10^5$ cells/ml.

Other culture conditions such as culturing temperature and $CO_2$ concentration in the floating culture can be set as appropriate. Culturing temperature is not subject to limitation; it can be, for example, about 30 to 40° C., preferably about 37° C. Also, the $CO_2$ concentration is, for example, about 1 to 10%, preferably about 5%.

Specifically, floating-culture include a method in which embryonic stem cells treated for dispersion after culturing the embryonic stem cells for maintenance is suspended in an appropriate medium (e.g., a medium produced by adding 5% KSR, 5 ml of 100× non-essential amino acids solution, 5 ml of 100× pyruvic acid and 0.5 ml of $1\times10^{-1}$ M 2-mercaptoethanol to 500 ml of Glasgow MEM medium. Optionally, it may comprise factors and the like described below.), the suspension is seeded at a cell density of $1\times10^4$-$5\times10^8$ of cells/ml into a cell-nonadhesive culture vessel, and then the cells are cultured at 37° C. for at least five days in a stream of 5% of carbon dioxide in a $CO_2$ incubator.

After the floating culture, the aggregate is kept as is, or dispersed (for example, trypsin/EDTA treatment), and then the cells may be further cultured under adhesion conditions (hereinafter abbreviated as adhesion culture as required). In the adhesion culture, it is preferable to use a cell-adhesive culture vessel, for example, a culture vessel coated with an extracellular matrix and the like (for example, poly-D lysine, laminin, fibronectin). Also, culture conditions such as culturing temperature and $CO_2$ concentration in the adhesion culture can easily be determined by those skilled in the art.

In the floating culture and adhesion culture, known differentiation induction substances can be used in combination. For example, for differentiation-inducing nervous system cells from embryonic stem cells, known substances that induce differentiation into nervous system cells can be used in combination. As examples of such differentiation induction substances, NGF (Biochem. Biophys. Res. Commun., 199, 552 (1994)), retinoic acid (Dev. Biol., 168, 342 (1995); J. Neurosci., 16, 1056 (1996)), BMP inhibitory factor (Nature, 376, 333-336 (1995)), and IGF (Genes & Development, 15, 3023-8 (2003)) can be mentioned. Also, for differentiation-inducing sensory organ cells from embryonic stem cells, known substances that induce differentiation into sensory organ cells can be used in combination. As examples of such differentiation induction substances, FGF, Shh, serum and the like can be mentioned.

According to the above-described method of floating culture and the combined method of floating culture and adhesion culture, by setting the length of cultivation and the like as appropriate, differentiated cells of ectodermal cells and the like can be obtained from embryonic stem cells. However, by further combining the methodologies described below as appropriate, nervous system cells and sensory organ cells can be differentiation-induced more efficiently.

(3.1. Induction of Differentiation into Nervous System Cells)

Referring to induction of differentiation into forebrain neurons and cerebellar neurons as examples of nervous system cells, methodologies to be combined for performing more suitable floating culture are described in detail below.

(3.1.1. Induction of Differentiation into Forebrain Neurons)

Forebrain neurons can be differentiation-induced from embryonic stem cells by the above-described floating culture, or, as required, by combining the above-described floating culture and adhesion culture. Preferably, from the viewpoint of improvement and stabilization of forebrain neuron differentiation efficiency, and the like, the methodologies described below can be used in combination.

One methodology is floating culture of embryonic stem cells in a serum-free medium substantially not comprising one, preferably two, more preferably all, selected from the group consisting of fibroblast growth factor (FGF), retinoic acid (RA) and a BMP signal promoter, or in a serum-free medium wherein one, preferably two, more preferably all, selected from the group consisting of FGF, RA and a BMP signal promoter, have been substantially inactivated. This methodology is useful in, for example, promoting differentiation into forebrain neurons (particularly telencephalic neurons).

The BMP signal promoter is not subject to limitation, as long as it is capable of enhancing the signal transduction mediated by BMP. As examples of the BMP signal promoter, a protein belonging to the BMP family (for example, BMP2, BMP4, BMP7, GDF), a BMP receptor, and the Smad protein can be mentioned. Preferably, the BMP signal promoter desired not to contaminate the serum-free medium is BMP4.

The serum-free medium substantially not comprising one, preferably two, more preferably all, selected from the group consisting of FGF, RA and a BMP signal promoter, refers to a serum-free medium not at all comprising one, preferably two, more preferably all, selected from the group consisting of FGF, RA and a BMP signal promoter, or a serum-free medium comprising these factors in amounts that do not have an adverse effect on the formation of a floating aggregate of embryonic stem cells and/or the cultivation of the aggregate (for example, cultivation intended for differentiation induction). Such a serum-free medium can be prepared by, for example, not adding the above-described factors as medium ingredients, or removing the above-described factors from the medium comprising the above-described factors (for example, use of anti-FGF antibody, anti-RA antibody, or anti-BMP antibody).

The serum-free medium wherein one, preferably two, more preferably all, selected from the group consisting of FGF, RA and a BMP signal promoter, have been substantially inactivated, refers to a serum-free medium wherein the activities of FGF, RA and a BMP signal promoter have been lost to the extent that does not have an adverse effect on the formation of a floating aggregate of embryonic stem cells and/or the cultivation of the aggregate, by the addition of inhibitors to a serum-free medium comprising the above-described factors. Such a serum-free medium can be prepared by adding appropriate amounts of inhibitors of FGF, RA, or a BMP signal promoter to the medium. As examples of the FGF inhibitor, anti-FGF antibody, soluble FGF receptors, and FGF receptor inhibitors (for example, Su5402) can be mentioned. As examples of the RA inhibitor, anti-RA antibody, soluble RA receptors, and RA receptor inhibitors can be mentioned. As examples of the BMP signal inhibitor, anti-BMP antibody, soluble BMP receptors, and BMP receptor inhibitors can be mentioned.

In floating culture of embryonic stem cells, it is of course possible to use a serum-free medium comprising FGF, RA, and a BMP signal promoter, or a serum-free medium wherein FGF, RA, and a BMP signal promoter have not been inactivated. Also, it is also possible to switch these culture conditions during the floating culture.

Another methodology is floating culture of embryonic stem cells in the presence of a Nodal signal inhibitor and/or a Wnt signal inhibitor. This methodology is useful in, for example, improving and stabilizing the efficiency of differentiation into forebrain neurons (particularly telencephalic neurons). Also, by using a Nodal signal inhibitor and a Wnt signal inhibitor in combination, a still more remarkable effect is expectable.

The Nodal signal inhibitor is not subject to limitation, as long as it is capable of suppressing the signal transduction mediated by Nodal. As examples of the Nodal signal inhibitor, Lefty-A, Lefty-B, Lefty-1, Lefty-2, soluble Nodal receptors, Nodal antibody, and Nodal receptor inhibitors can be mentioned, with preference given to Lefty-A.

The concentration of Nodal signal inhibitor used in the floating culture can be a concentration that enables the promotion of the neural differentiation of a floating aggregate, or the accomplishment of the above-described utility. This concentration can be, for example, about 0.1 to 100 µg/ml, preferably about 0.5 to 50 µg/ml, more preferably about 1.0 to 10 µg/ml, most preferably about 5 µg/ml, for Lefty.

Although the Nodal signal inhibitor may be added to the medium already at the start of cultivation of embryonic stem cells, it may be added to the medium after several days of cultivation (for example, at a time within 10 days of cultivation). Preferably, the Nodal signal inhibitor is added to the medium at a time within 5 days of cultivation.

The Wnt signal inhibitor is not subject to limitation, as long as it is capable of suppressing the signal transduction mediated by Wnt. As examples of the Wnt signal inhibitor, Dkk1, the Cerberus protein, Wnt receptor inhibitors, soluble Wnt receptors, Wnt antibody, casein kinase inhibitors, and the dominant negative Wnt protein can be mentioned, with preference given to Dkk1 or the Cerberus protein.

The concentration of Wnt signal inhibitor used in the floating culture can be a concentration that enables the promotion of the neural differentiation of a floating aggregate, or the accomplishment of the above-described utility. This concentration can be, for example, about 0.05 to 20 µg/ml, preferably about 0.1 to 10 µg/ml, more preferably about 0.5 to 5.0 µg/ml, most preferably about 1 µg/ml, for Dkk1.

Although the Wnt signal inhibitor may be added to the medium already at the start of cultivation of embryonic stem cells, it may be added to the medium after several days of cultivation (for example, at a time within 10 days of cultivation). Preferably, the Wnt signal inhibitor is added to the medium at a time within 5 days of cultivation.

It is of course possible to perform floating culture of embryonic stem cells in the absence of a Nodal signal inhibitor and/or a Wnt signal inhibitor. It is also possible to switch these culture conditions during the floating culture.

Still another methodology is floating culture of embryonic stem cells in a serum-free medium substantially not comprising a Nodal signal promoter and/or a Wnt signal promoter, or a serum-free medium wherein a Nodal signal promoter and/or a Wnt signal promoter has been substantially inactivated. This methodology is useful in, for example, promoting differentiation into forebrain neurons (particularly telencephalic neurons).

The serum-free medium substantially not comprising a Nodal signal promoter and/or a Wnt signal promoter refers to a serum-free medium not at all comprising a Nodal signal promoter and/or a Wnt signal promoter, or a serum-free medium comprising a Nodal signal promoter and/or a Wnt signal promoter in an amount that does not have an adverse effect on the formation of a floating aggregate of embryonic stem cells and/or the cultivation of the aggregate (for example, cultivation intended for differentiation induction). A serum-free medium substantially not comprising a Nodal signal promoter and/or a Wnt signal promoter can be prepared by, for example, not adding a Nodal signal promoter and/or a Wnt signal promoter as a medium ingredient, or removing a Nodal signal promoter and/or a Wnt signal promoter from the medium comprising the Nodal signal promoter and/or the Wnt signal promoter.

Also, the serum-free medium wherein a Nodal signal promoter and/or a Wnt signal promoter has been substantially inactivated refers to a serum-free medium wherein the activity of a Nodal signal promoter and/or a Wnt signal promoter has been lost to the extent that does not have an adverse effect on the formation of a floating aggregate of embryonic stem cells and/or the cultivation of the aggregate, by the addition of a Nodal signal inhibitor and/or a Wnt signal inhibitor to a serum-free medium comprising a Nodal signal promoter and/or a Wnt signal promoter.

The Nodal signal promoter is not subject to limitation, as long as it is capable of enhancing the signal transduction mediated by Nodal. As examples of the Nodal signal promoter, Nodal, a protein belonging to the TGFβ family (for example, activin), the Smad protein, and active Nodal receptors can be mentioned. Preferably, the Nodal signal promoter desired not to contaminate the serum-free medium is Nodal.

The Wnt signal promoter is not subject to limitation, as long as it is capable of enhancing the signal transduction mediated by Wnt. As examples of the Wnt signal promoter, a protein belonging to the Wnt family (for example, Wnt1 to 16), a GSK3 inhibitor, a Wnt receptor, and the $Li^+$ ion can be mentioned. Preferably, the Wnt signal promoter desired not to contaminate the serum-free medium is Wnt3a.

It is of course possible to perform floating culture of embryonic stem cells in the presence of a Nodal signal promoter and/or a Wnt signal promoter. It is also possible to switch these culture conditions during the floating culture.

Still another methodology is to continue floating culture for at least 5 days. This methodology is useful in, for example, promoting differentiation into forebrain neurons (particularly telencephalic neurons). Even in the case of cultivation for less than 5 days, it is of course possible to differentiation-induce forebrain neurons more efficiently than conventional methods.

Still yet another methodology is floating culture of embryonic stem cells in the presence of an Shh signal promoter. This methodology is useful in, for example, promoting differentiation into ventral telencephalic neurons, and in suppressing differentiation into dorsal telencephalic neurons.

The Shh signal promoter is not subject to limitation, as long as it is capable of enhancing the signal transduction mediated by Shh. As examples of the Shh signal promoter, a protein belonging to the Hedgehog family (for example, Shh), an Shh receptor, and an Shh receptor agonist can be mentioned, with preference given to Shh.

The concentration of Shh signal promoter used in the floating culture can be a concentration that enables the accomplishment of the above-described utility. This concentration can be, for example, about 1.0 to 1000 nM, preferably about 5.0 to 500 nM, more preferably about 10 to 500 nM, most preferably about 30 to 300 nM.

Although the Shh signal promoter may be added to the medium already at the start of cultivation of embryonic stem cells, it can be added to the medium for example, at Day 2 of floating culture or thereafter, preferably at Day 4 of floating culture or thereafter.

It is of course possible to perform floating culture of embryonic stem cells in the absence of an Shh signal promoter. It is also possible to switch this culture condition during the floating culture.

Still another methodology is floating culture of embryonic stem cells in the presence of a Shh signal inhibitor. By the addition of an Shh signal promoter, promotion of the differentiation of embryonic stem cells into ventral forebrain neurons, suppression of the differentiation of embryonic stem cells into dorsal forebrain neurons, and the like are expected. Therefore, using an Shh signal inhibitor, it is considered that effects such as suppression of ventral forebrain neuron differentiation and promotion of dorsal forebrain neuron differentiation are expectable.

The Shh signal inhibitor is not subject to limitation, as long as it is capable of enhancing the signal transduction mediated by Shh. As examples of the Shh signal inhibitor, an antibody against the Shh signal promoter, a dominant negative mutant of the Shh signal promoter, a soluble Shh receptor, and an Shh receptor antagonist can be mentioned, with preference given to an Shh antibody and an Shh dominant negative mutant.

It is of course possible to perform floating culture of embryonic stem cells in the absence of an Shh signal inhibitor. It is also possible to switch this culture condition during the floating culture.

Still another methodology is to perform adhesion culture following floating culture of embryonic stem cells. After the aggregate is kept as is, or after dispersion treatment (for example, trypsin/EDTA treatment), the cells can be subjected to adhesion culture. In adhesion culture, it is preferable to use a cell-adhesive culture vessel, for example, a culture vessel coated with an extracellular matrix and the like (for example, poly-D lysine, laminin, fibronectin). Adhesion culture can be performed for, for example, 1 day or more, preferably 1 to 14 days, more preferably 2 to 5 days.

Still yet another methodology is to perform adhesion culture following floating culture in the presence of a Wnt signal promoter. This methodology is useful in, for example, promoting differentiation into dorsal telencephalic neurons, and in suppressing differentiation into ventral telencephalic neurons.

As examples of the Wnt signal promoter used in adhesion culture following floating culture, a protein belonging to the Wnt family (for example, Wnt3a), a GSK3 inhibitor, a Wnt receptor, the Li$^+$ ion and the like can be mentioned, with preference given to Wnt3a.

The concentration of Wnt signal promoter used in the adhesion culture after floating culture is not subject to limitation, as long as it is a concentration that enables the accomplishment of the above-described utility; for example, this concentration can be about 0.1 to 500 ng/ml, preferably about 1.0 to 100 ng/ml, more preferably about 5.0 to 50 ng/ml, most preferably about 50 ng/ml, for Wnt3a.

The Wnt signal promoter may be added to the medium already at the start of the adhesion culture, and may be added to the medium between just after the start of the adhesion culture and several days later (for example, 4 days after the start of the adhesion culture and thereafter, or at a time within 5 days of the adhesion culture). Preferably, the Wnt signal promoter is added to the medium at a time within 5 days of the adhesion culture.

The above-described various methodologies can be combined as appropriate in order to efficiently obtain forebrain neurons, or particular forebrain neurons (for example, telencephalic neurons, ventral telencephalic neurons, dorsal telencephalic neurons). For example, by combining methodologies showing the same effect, a better effect is expectable.

(3.1.2. Induction of Differentiation into Cerebellar Neurons)

Cerebellar neurons can be differentiation-induced from embryonic stem cells by the above-described floating culture, or, as required, by combining the above-described floating culture and adhesion culture. Preferably, from the viewpoint of improving the efficiently of differentiation into cerebellar neurons and the like, the methodologies described below can be used in combination.

One methodology is floating culture of embryonic stem cells in a serum-free medium substantially not comprising FGF and/or RA, or a serum-free medium wherein FGF and/or RA has been substantially inactivated. This methodology is useful in, for example, promoting differentiation into cerebellar neurons. Details of this methodology are as described above.

Another methodology is to continue floating culture for at least 5 days. This methodology is useful in, for example, promoting differentiation into cerebellar neurons. Even in the case of cultivation for less than 5 days, it is of course possible to differentiate-induce cerebellar neurons more efficiently than conventional methods.

Still another methodology is floating culture of embryonic stem cells in the presence of a Wnt signal promoter. This methodology is useful in, for example, promoting differentiation into cerebellar neurons, and particularly into particular cerebellar neurons (for example, cerebellar granule cells, cerebellar Purkinje's cells). The Wnt signal promoter is the same as described above.

The concentration of Wnt signal promoter used in the floating culture can be a concentration that enables the accomplishment of the above-described utility. This concentration can be, for example, about 0.1 to 1000 ng/ml, preferably about 1.0 to 100 ng/ml, more preferably about 2.0 to 50 ng/ml, most preferably about 5.0 to 50 ng/ml, for Wnt3a.

Although the Wnt signal promoter may be added to the medium already at the start of cultivation of embryonic stem cells, it may be added to the medium after several days of cultivation. For example, the Wnt signal promoter is added to the medium at a time after 5 to 10 days of cultivation, preferably at a time after 5 to 8 days.

It is of course possible to perform floating culture of embryonic stem cells in the absence of a Wnt signal promoter. It is also possible to switch these culture conditions during the floating culture.

Still yet another methodology is floating culture of embryonic stem cells in the presence of a BMP signal promoter. This methodology is useful in promoting differentiation into cerebellar neurons, and into particular cerebellar neurons (for example, cerebellar granule cells, cerebellar Purkinje's cells). The BMP signal promoter is the same as described above.

The concentration of BMP signal promoter used in the floating culture can be a concentration that enables the accomplishment of the above-described utility. This concentration can be, for example, about 0.01 to 100 nM, preferably about 0.05 to 10 nM, more preferably about 0.1 to 1.0 nM, most preferably about 0.5 to 1.0 nM, for BMP4.

Although the BMP signal promoter may be added to the medium already at the start of cultivation of embryonic stem cells, it may be added to the medium after several days of cultivation. For example, the BMP signal promoter is added to the medium at a time after 5 to 10 days of cultivation, preferably at a time after 5 to 8 days.

It is of course possible to perform floating culture of embryonic stem cells in the absence of a BMP signal promoter. It is also possible to switch this culture condition during the floating culture.

Also, in order to enable efficient differentiation into cerebellar neurons, particularly into cerebellar granule cells or cerebellar Purkinje's cells, the above-described two methodologies can be combined. That is, floating culture of embryonic stem cells in the presence of a Wnt signal promoter and a BMP signal promoter is also preferable.

Still another methodology is floating culture of embryonic stem cells in the presence of FGF. Although FGF may be added to the medium already at the start of cultivation of embryonic stem cells, it may be added to the medium after several days of cultivation. For example, FGF is added to the medium at a time at 4 to 12 days of cultivation, preferably 5 to 10 days. It is of course possible to perform floating culture of embryonic stem cells in the absence of FGF. It is also possible to switch this culture condition during the floating culture.

The concentration of FGF used in the floating culture can be a concentration that enables the accomplishment of the above-described utility. This concentration can be, for example, about 0.1 to 500 ng/ml, preferably about 1 to 200 ng/ml, more preferably about 10 to 200 ng/ml, most preferably about 20 to 100 ng/ml, for FGF8b.

In order to enable efficient differentiation into cerebellar neurons, particularly into cerebellar Purkinje's cell, the above-described methodologies can be combined. That is, floating culture of embryonic stem cells in the presence of a BMP signal promoter and FGF (for example, FGF8 such as FGF8b) is also preferable.

Still yet another methodology is to perform adhesion culture following floating culture of embryonic stem cells. After the aggregate is kept as is, or after dispersion treatment (for example, trypsin/EDTA treatment), the cells can be subjected to adhesion culture. For example, for promoting the differentiation into cerebellar Purkinje's cells, the aggregate as is may be subjected to adhesion culture. In adhesion culture, it is preferable to use a cell-adhesive culture vessel, for example, a culture vessel coated with an extracellular matrix and the like (for example, poly-D lysine, laminin, fibronectin) Adhesion culture can be performed for, for example, 1 day or more, preferably 1 to 20 days, more preferably 5 to 20 days, most preferably 10 to 15 days.

The above-described various methodologies can be combined as appropriate in order to efficiently obtain cerebellar neurons, or particular cerebellar neurons (for example, cerebellar granule cells, cerebellar Purkinje's cells). For example, by combining methodologies showing the same effect, a better effect is expectable.

Also, the cerebellar neurons obtained can be further differentiated. For example, after Math1$^+$ cells are separated as described in Example 9, further differentiation can be induced by aggregating and co-culturing them with dispersed cells of the mammalian fetal or neonatal cerebellum (Development 106, 441-447 (1989); Development 128, 3133-3144 (2001)). For example, by this method, cerebellar granule cells showing the characteristic of being able to migrate in adhesion to parallel fiber axons and/or the characteristic of elongating T-shaped axons are obtained (these are characteristics of cerebellar granule cells).

As described above, the method of the present invention is highly useful for enabling the differentiation induction into various nervous system cells.

(3.2. Induction of Differentiation into Sensory Organ Cells)

Sensory organ cells can be differentiation-induced from embryonic stem cells by the above-described floating culture, or, as required, by a combination of the above-described floating culture and adhesion culture. Preferably, from the viewpoint of improving the efficiency of differentiation into sensory organ cells and the like, the methodologies described below can be used in combination.

One methodology is floating culture of embryonic stem cells in a serum-free medium substantially not comprising one, preferably two, more preferably all, selected from the group consisting of FGF, RA, and a BMP signal promoter, or a serum-free medium wherein one, preferably two, more preferably all, selected from the group consisting of FGF, RA and a BMP signal promoter, have been substantially inactivated. This methodology is useful in, for example, promoting differentiation into sensory organ cells. Details of this methodology are as described above.

Another methodology is to continue floating culture for at least 5 days. This methodology is useful in, for example, promoting differentiation into sensory organ cells. Even in the case of cultivation for less than 5 days, it is of course possible to differentiation-induce sensory organ cells more efficiently than conventional methods.

Still another methodology is the addition of serum to a serum-free medium comprising a floating aggregate of embryonic stem cells (cultured for several days). This methodology is useful in, for example, promoting differentiation into sensory organ cells (for example, retinal cells, visual cells).

Regarding the serum, a serum derived from an optionally chosen animal, preferably from a mammal, can be used. The mammal from which the serum is derived is the same as the mammal from which the embryonic stem cells are derived (described above). Although the serum concentration is not subject to limitation, as long as it is a concentration enabling the efficient differentiation into sensory organ cells; it can be, for example, about 0.5 to 30%, preferably about 1.0 to 20%, more preferably about 3 to 10%, most preferably about 5%.

The timing of addition of serum to a serum-free medium comprising a floating aggregate of embryonic stem cells is not subject to limitation, as long as it enables differentiation into sensory organ cells; for example, it is within 3 to 7 days after the start of floating culture. Differentiation into sensory organ cells is possible in the absence of serum. It is also possible to switch the condition whether serum is present or not during the floating culture.

Still yet another methodology is the addition of an Shh signal promoter to a serum-free medium comprising a floating aggregate of embryonic stem cells (cultured for several days). This methodology is useful in, for example, promoting differentiation into sensory organ cells (for example, retinal cells, visual cells). The Shh signal promoter is the same as described above.

The concentration of Shh signal promoter used in the floating culture is not subject to limitation, as long as it enables the promotion of differentiation into sensory organ cells; it can be, for example, about 0.1 to 500 nM, preferably about 0.5 to 100 nM, more preferably about 1.0 to 50 nM, most preferably about 3.0 to 30 nM.

The timing of addition of an Shh signal promoter to a serum-free medium comprising a floating aggregate of embryonic stem cells is not subject to limitation, as long as it enables differentiation into sensory organ cells; for example, it is within 7 days (for example, 3 to 7 days) after the start of floating culture. Differentiation into sensory organ cells is also possible in the absence of an Shh signal promoter. It is also possible to switch the condition whether an Shh signal promoter is present or not during the floating culture.

Still another methodology is floating culture of embryonic stem cells in the presence of a Nodal signal promoter such as Nodal or activin. This methodology is useful in, for example, promoting differentiation into sensory organ cells (for example, retinal cells, visual cells). The Nodal signal promoter is the same as described above.

The concentration of Nodal signal promoter used in the floating culture can be a concentration enabling the more efficient production of sensory organ cells. This concentration can be, for example, about 1 to 10000 ng/ml, preferably about 10 nM to 1000 ng/ml, more preferably about 20 to 500 ng/ml, most preferably about 50 to 200 ng/ml.

The timing of addition of a Nodal signal promoter to a serum-free medium comprising a floating aggregate of embryonic stem cells is not subject to limitation, as long as it enables differentiation into sensory organ cells; for example, it is within 7 days (for example, after 3 to 7 days) after the start of floating culture. Differentiation into sensory organ cells is also possible in the absence of a Nodal signal promoter. It is also possible to switch the condition whether a Nodal signal promoter is present or not during the floating culture.

Also, to enable efficient differentiation into sensory organ cells, the above-described three methodologies can be combined. That is, a combination of serum and an Shh signal promoter, a combination of serum and a Nodal signal promoter, a combination of an Shh signal promoter and a Nodal signal promoter, and a combination of serum, an Shh signal promoter and a Nodal signal promoter, are also preferable.

Still yet another methodology is floating culture of embryonic stem cells in the presence of a Wnt signal inhibitor such as Dkk1 and/or a Nodal signal inhibitor such as Lefty-A. This methodology is useful in, for example, promoting differentiation into sensory organ cells (for example, retinal cells, visual cells). A combination of these methodologies is also preferable. The Wnt signal inhibitor and the Nodal signal inhibitor are the same as described above.

The concentration of Wnt signal inhibitor used in the floating culture can be a concentration that enables the accomplishment of the above-described utility. This concentration can be, for example, about 0.01 to 100 µg/ml, preferably about 0.1 to 10 µg/ml, more preferably about 0.5 to 5.0 µg/ml, most preferably about 1.0 µg/ml, for Dkk1.

The concentration of Nodal signal inhibitor used in the floating culture can be a concentration that enables the accomplishment of the above-described utility. This concentration can be, for example, about 0.01 to 20 µg/ml, preferably about 0.05 to 5 µg/ml, more preferably about 0.1 to 1.0 µg/ml, most preferably about 0.5 µg/ml, for Lefty-A.

A Wnt signal inhibitor and a Nodal signal inhibitor may be added to the medium already at the start of floating culture of embryonic stem cells, and can be added to the medium, for example, at a time within 5 days after the start of cultivation. Of course, these inhibitors may be added to the medium at different times.

Also, to particularly efficiently perform differentiation into sensory organ cells (for example, retinal cells, visual cells), floating culture of embryonic stem cells in the presence of a combination of certain factors, for example, Lefty (for example, Lefty-A), Dkk1, serum and activin, is preferable.

It is of course possible to perform floating culture of embryonic stem cells in the absence of a Wnt signal inhibitor and/or a Nodal signal inhibitor. It is also possible to switch this culture condition during the floating culture.

Still another methodology is to perform adhesion culture after floating culture of embryonic stem cells. After the aggregate is kept as is, or after dispersion treatment (for example, trypsin/EDTA treatment), the cells can be subjected to adhesion culture. In the adhesion culture, it is preferable to use a cell-adhesive culture vessel, for example, a culture vessel coated with an extracellular matrix and the like (for example, poly-D lysine, laminin, fibronectin). The length of adhesion culture can be, for example, 1 day or more.

Still yet another methodology is to perform long-term cultivation under adhesion conditions after floating culture. This methodology is useful in promoting differentiation into sensory organ cells, particularly into visual cells. The length of long-term cultivation is not subject to limitation, as long as it enables differentiation into sensory organ cells; it can be, for example, 3 days or more, preferably 5 to 25 days, more preferably 7 to 20 days, most preferably 7 to 18 days.

The above-described various methodologies can be combined as appropriate in order to efficiently obtain sensory organ cells or particular sensory organ cells (for example, retinal system cells, visual cells). For example, by combining methodologies showing the same effect, a better effect is expectable.

As described above, the method of the present invention is highly useful for enabling the induction of differentiation into various sensory organ cells.

(4. Cell Culture and its Use as a Pharmaceutical)

The present invention also provides a cell culture obtained by the method of the present invention. The cell culture of the present invention can be, for example, a floating aggregate of embryonic stem cells, cells obtained by dispersing the floating aggregate, cells obtained by culturing the dispersed cells, and the like. Also, the present invention provides homogeneous cells isolated or purified from such a cell culture to the extent that enables its administration to a subject, for example, forebrain neurons such as telencephalic neurons, nervous system cells such as cerebellar neurons, and sensory organ neurons such as retinal precursor cells.

The cells obtained by the method of the present invention can be used as therapeutic agents for diseases caused by disorder of nervous system cells, for example, forebrain neurons, and of sensory organ cells, or for supplementing for the cells in a state of cell damage due to other causes, and the like. As examples of the diseases caused by disorder of nervous system cells, Parkinson's disease, spinocerebellar degeneration, Huntington's disease, Alzheimer's disease, ischemic cerebral diseases (for example, cerebral stroke), epilepsy, cerebral trauma, spinal injury, motor nerve disease, neurodegenerative disease, pigmentary degeneration of retina, senile macular degeneration, inner ear hearing loss, multiple sclerosis, amyotrophic lateral sclerosis, diseases caused by damage due to neurotoxins, and the like can be mentioned. Specifically, as examples of the disease caused by the disorder of forebrain neurons, particularly telencephalic neurons, Huntington's diseases, Alzheimer's disease, ischemic cerebral diseases (for example, cerebral stroke), and cerebral trauma can be mentioned. Also, as examples of the disease caused by the disorder of cerebellar neurons, spinocerebellar degeneration, alcoholic cerebellar degeneration, and trauma in the cerebellum can be mentioned. Also, as the disease caused by the disorder of sensory organ cells, pigmentary degeneration of retina, macular degeneration, glaucoma, and diabetic retinopathy can be mentioned. Furthermore, as a state wherein supplementation for these cells is desired, post-neurosurgery (for example, post-brain tumor extirpation) can be mentioned.

Furthermore, when the cells such as nervous system cells or sensory cells, obtained by the method of the present invention are used as a therapeutic agent for diseases caused by the disorder of said cells, it is preferred that the cells are transplanted into a subject after increasing purity of the cells.

Any one of the already known methods for separating and purifying cells can be used as the method for increasing purity of cells. Examples include a method using a flow cytometer (see, e.g., Antibodies—A Laboratory Manual, Cold Spring Harbor Laboratory (1988); Monoclonal Antibodies: principles and practice, Third Edition, Acad. Press (1993); Int. Immunol., 10, 275 (1998)), Panning method (see, e.g., Monoclonal Antibodies: principles and practice, Third Edition, Acad. Press (1993); Antibody Engineering, A Practical Approach, IRL Pressat Oxford University Press (1996); J. Immunol., 141, 2797 (1988)) and a cell fractionation method using density difference of sucrose concentration (see, e.g., Techniques of Tissue Culture (Third Edition), Asakura Shoten (1996)).

The method for increasing purity of differentiated cells of the present invention comprises culturing the cells such as nervous system cells or sensory cells, obtained by inducing differentiation of the embryonic stem cells as described above, in a medium comprising an anticancer agent. Since cells under an undifferentiated state can be removed by this step, and differentiated cells can be obtained with further higher purity, so that it becomes more suitable as a pharmaceutical agent. That is, by the treatment with an anticancer agent, cells other than the differentiated cells of interest, such as undifferentiated cells, can be removed.

Here, the anticancer agents include mitomycin C, 5-fluorouracil, adriamycin, ara-C, methotrexate and the like. It is preferable to use these anticancer agents at a concentration which shows stronger cytotoxicity on undifferentiated cells than that on differentiated cells. Specifically, the optimum concentration can be determined by carrying out culturing with these anticancer agents according to the method described above, such as a method in which culturing is carried out at 37° C. for several hours, preferably 2 hours, in a stream of 5% carbon dioxide in a $CO_2$ incubator, using a medium comprising any of these anticancer agents at a concentration of 1/100 to 1 equivalent of the concentration used in the living body described in the Pharmacopoeia of Japan.

Any medium can be used in this method, so long as it is capable of culturing differentiation-induced cells. Specifically, the medium described above and the like can be mentioned.

In addition, in the transplantation medical treatment, rejection due to difference in the histocompatibility antigens sometimes causes a problem, but this problem can be resolved by using the embryonic stem cell into which the nucleus of a somatic cell has been transplanted, or the embryonic stem cell in which a gene on the chromosome has been modified.

Furthermore, cells such as nervous system cells or sensory cells, which is from a somatic cell-donated individual can be obtained by carrying out induction of the differentiation using the embryonic stem cell into which the nucleus of a somatic cell has been transplanted. Such a cell of individual is useful not only as a transplantation medical treatment of the cell itself but also as a diagnosing material for judging whether or not an existing drug is effective for the individual. Also, since sensitivities to oxidation stress and aging can be judged by culturing a differentiation-induced cell for a prolonged period of time, risk of individual for a disease such as a neurodegenerative disease can be evaluated by comparing its function and life with those of a cell derived from other individual, and the evaluation data are useful for providing an effective method for preventing a disease which is diagnosed as high in its future morbidity rate.

The cells such as nervous system cells, which are differentiation-induced from the embryonic stem cells can be transplanted to diseased parts of the body of a patient by a method known per se (see, e.g., Nature Neuroscience, 2, 1137 (1999)).

The present invention is hereinafter described in more detail by means of the following examples, which, however, merely show illustration and are not to be construed as limiting scope of the present invention.

EXAMPLES

Example 1

Floating-Culture of ES Cells Aggregates in the Absence of Serum 1.1. Analysis of EB5-Cells by Floating Culture First, EB5 cells (Nature Genet., Vol. 24: 372 (2000)), mouse ES cells (derived from E14) were cultured using serum-free floating aggregate (SFEB: Serum-free Floating culture of Embryoid body-like Aggregates) method.

Specifically, As ES cells, those cultured for maintenance by conventional culture method without feeder cells supplemented with 1% fetal calf serum, 10% KSR (Knockout Serum Replacement), and LIF were used for SFEB method (see, Neuron, Vol. 28: 31-40 (2000)). Next, after ES cell colonies were subjected to trypsin/EDTA treatment to make single cells, 10 ml of the cells ($6 \times 10^4$ cells/ml) were seeded on cell non-adhesive culture plastic plate (diameter: 10 cm), and incubated at 37° C., 5% $CO_2$ for five days. As medium, differentiation medium composed of 500 ml of GMEM, 5 ml of 100×NEAA, 5 ml of 100×pyruvate, and 0.5 ml of $1 \times 10^{-1}$ M 2-mercaptoethanol, and 5% KSR (Knockout Serum Replacement). Moreover, EB5 cells were cultured under adhesion with similar conditions except use of gelatin-coated culture dish, and used as control.

As a result, when ES cells were cultured as floating aggregates by SFEB method, ES cells grew well, and generated a large number of NCAM⁺ cells (>60%; analyzed by immunostaining method). In control of cultured under adhesion, however, single ES cells formed only a few, small colonies, in which NCAM⁺ cells occupied minor populations (<20%).

1.2. Analysis of Mouse ES Cells from Mouse Introduced with Reporter Gene by Floating Culture Next, For quantitative analysis, mouse ES cells wherein GFP (green fluorescent protein) was knocked in the nerve marker Sox1 gene by homologous recombination (hereinafter abbreviated as Sox1/GFP-mES cells as required; see Nature Biotechnology Vol. 21: 183-186 (2003)) were cultured by the SFEB method. The culture conditions were the same as those for the SFEB method described in 1.1. above except that Sox1/GFP-mES cells were used as the ES cells.

As a result, FACS analysis showed that Sox1/GFP⁺-mES cells increased during days 3-5, while E-cadherin⁺cells decreased gradually over the first 5 days. A similar observation was also obtained by immunostaining studies. Furthermore, after 5 days of SFEB method, 60-85% of cells became Sox1-GFP positive, the percentage of Sox1-GFP⁺ populations were high when the culture was started at the range of $3 \times 10^4$-$1 \times 10^5$ initial cells/ml.

From the above 1.1. and 1.2., it is indicated that, when cultured under appropriate conditions, ES cells aggregates efficiently and generate nervous system cells quickly in the absence of serum and feeder cells.

Example 2

Inhibition of Endogenous Nodal and Wnt Signals Further Improves the Efficiency of Differentiation of ES Cells into Nervous System Cells by the SFEB Method Next, to further improve the efficiency of differentiation into nervous system cells by the SFEB method, the present inventors attempted to determine whether or not the efficiency of differentiation into nervous system cells was improved by inhibiting Nodal, Wnt, and BMP, which are promoters of differentiation into mesodermal cells. Lefty-A (manufactured by R&D Company) as the anti-Nodal reagent, Dkk1 (manufactured by R&D Company) as the anti-Wnt reagent, and BMPRIA-Fc receptobody (manufactured by R&D Company) as the anti-BMP reagent, were added to the differentiation medium on Day 0 of cultivation by the SFEB method. Moreover, the concentrations used are 5 μg/ml of Lefty-A, 1 μg/ml of Dkk1 and 1.5 μg/ml of BMPRIA-Fc receptobody respectively.

As a result, the addition of Lefty-A or Dkk1 was found to evaluate the frequency of Sox1-GFP⁺ cells. Additionally, in the method of the above-described 1.2., the absolute value of GFP expression varied by about 10-15% from experiment to experiment even under condition in which initial cell density is $5 \times 10^4$ cell/ml, however, the addition of Lefty-A or Dkk1 unexpectedly stabilized the value of GFP expression. Furthermore, combined use of Lefty-A and Dkk1 significantly increased the frequency of Sox1-GFP⁺ cells to about 90%. Interestingly, even when initial cell density is high ($2 \times 10^5$ cells/ml), the combined use kept Sox1-GFP⁺ cells high frequency (about 80%). In contrast, addition of BMPRIA-Fc receptobody did not significantly affect the frequency of Sox1-GFP⁺ cells.

Next, we tested effects of Nodal and Wnt by adding Nodal protein (manufactured by R&D) and Wnt3a protein (manufactured by R&D) to SFEB culture. As a result, it is confirmed that additions of the Nodal protein (5 μg/ml) and Wnt3a protein (50 ng/ml) during days 0-5 and days 2-5 significantly suppress the frequency of Sox1-GFP⁺ cells in SFEB method.

From the above, it is suggested that inhibition of Nodal or Wnt signal improves efficacy of differentiation of ES cells into nervous system cells, and the differentiation efficacy is stabilized, as well as inhibition of both Nodal and Wnt signals remarkably improves efficacy of differentiation of ES cells into nervous system cells.

Example 3

Analysis of Mechanisms Behind Neural Differentiation by the SFEB Method

Then, we tried to examine whether the predominant differentiation into nervous system cells by SFEB method was caused by some selective biases during the culture period or was caused by accumulation of direct differentiation into the neural fate.

Using TUNEL assay (Int. J. Oncology, 1, 639-648 (1992)), we first tested whether or not cell death in the non-neural population is enhanced during days 3 and 4 of the culture, when the proportion of Sox1-GFP⁺ cells as increasing.

As a result, the percentage of TUNEL⁺ apoptotic cells exhibited no significant differences between Sox1-GFP⁻ ($5.5 \pm 0.7\%$ on day 3 and $4.8 \pm 1.4\%$ on day 4, n=3) and Sox1-GFP⁺ ($4.8 \pm 0.9\%$ on day 3 and $4.6 \pm 1.5\%$ on day 4, n=3) populations, indicating that Sox1-GFP cells are not actively eliminated by apoptosis during culture by SFEB method.

Next, the present inventors compared cell proliferation parameters in Sox1-GFP⁻ and Sox1-GFP⁺ populations by BrdU uptake assay and phospho-histone H3 immunostaining assay.

As a result, percentage of BrdU-labeled cells (30 min exposure) showed less than 10% differences between Sox1-GFP⁻ ($45.3 \pm 0.4\%$ on day 3 and $40.9 \pm 1.2\%$ on day 4, n=3) and Sox1-GFP⁺ ($49.6 \pm 2.6\%$ on day 3 and $42.4 \pm 1.1\%$ on day 4, n=3) populations. A similar situation was observed with the ratios of phosphor-histone H3⁺ cells ($1.2 \pm 0.5\%$ on day 3 and $1.0 \pm 0.7\%$ on day 4 in Sox1-GFP⁻ population; $1.5 \pm 0.7\%$ on day 3 and $1.3 \pm 0.6\%$ on day 4 in Sox1-GFP⁺ population, n=3). These results indicate that the biased amplification does not play a major rule in highly efficient differentiation of ES cell into nervous system cells by SFEB method.

From the above, it is suggested that preferential neural differentiation by SFEB method is attributed to direct neural differentiation rather than to selective cell death or proliferation.

Example 4

The SFEB Method Allows ES Cells to Differentiate into Telencephalic Neurons at High Efficiency Mouse ES cells (EB5 cells) were subjected to serum-free floating culture by the SFEB method in the same manner as Example 1 for 5 days, after which they were dispersed by trypsin/EDTA treatment, seeded to a cell culture slide coated with poly-D lysine/laminin, and cultured in a differentiation medium (as described above) for 2 days, and then in a GMEM+N2 medium (composition: GMEM+1×N-2 Supplement (manufactured by Gibco, a supply of ×100 concentration was used after dilution), 0.1 mM non-essential amino acid, 1 mM sodium pyruvate, 0.1 mM 2-mercaptoethanol) for 3 days. The finally obtained differentiated cells were analyzed by the fluorescent antibody method using anti-Bf1 antibody. For comparison, neural differentiation from ES cells was performed by the SDIA method, and the cells obtained were analyzed by the fluorescent antibody method in the same manner.

As a result, about 15% cells of the differentiated cells by SFEB method are positive for Bf1 which is nucleoprotein specific to a telencephalic neural cell. On the other hand, in differentiated cells obtained by SDIA method, the percentage of Bf1$^+$ cells is low (about 1%).

Next, Expression of markers other than Bf1 was tried to examined. As antibodies to the makers, anti-Pax6 antibody (manufactured by DSHB), anti-Gsh2 antibody and anti-NRx2.1 antibody were used. Moreover, as anti-Gsh2 antibody and anti-NRx2.1 antibody, those produced myself by immunizing rabbit with synthetic peptide were used.

As a result, among Bf1$^+$ cells, about 40% cells expressed a marker (Pax6 positive) for dorsal cerebrum (cerebral cortex and the like are developed), and 25% cells expressed a marker (Gsh2 positive) for middle portion of ventral cerebrum (basal ganglion and the like are developed). Additionally, approximately 10% cells expressed NRx2.1 for most ventral side of telencephalon (hypothalamus and the like are developed).

From the above, it is revealed that the SFEB method can efficiently induce differentiation of ES cells into telencephalic neurons, and can induce differentiation of ES cells into cells in cerebral cortex, basal ganglion, hypothalamus and the like as telencephalic neurons.

Example 5

The First 5 Days of Cultivation are Important to the Differentiation of ES Cells into Telencephalic Neurons Highly efficient Differentiation of ES cells into Bf1$^+$ cells by SFEB method is extremely interesting. Therefore, difference in rates of differentiation into Bf1$^+$ cell by SFEB method and SDIA method was tried to determine in terms of time window.

As a result, Bf1$^+$ cells were generated at a high frequency (11%) when cultured by SFEB method for 5 days, and then cultured by SDIA method for additional five days. In contrast, few Bf1$^+$ cells were observed (<2%) when cultured by SDIA method for first five days, and cultured on laminin/poly-D-lysin/fibronectin-coated dishes for additional five days.

From the above, it is suggested that first five days during the induction period play a decisive role for efficient differentiation of ES cells into Bf1$^+$ cells.

Example 6

SFEB Method Induce Precursor Cells of Caudal Tissue by Using Combination with Treatment with Retinoic Acid Then, test was carried out using retinoic acid (RA) to examine effect of combined use of SEFA method and caudalizing factor. Moreover, SEFA method was carried out as similar to Example 1, and RA (manufactured by Sigma) was added to medium so as to become 0.2 µM after 3-5 days of the culture.

As a result, Bf1$^+$ cells were almost completely eliminated by caudalizing factor (<1% or less). Additionally, according to RT-PCR analysis, rostal markers Bf1 and Otx2 were completely suppressed in SFEB-induced neural cells by RA while the caudal marker Hoxb4 was induced.

From the above, combined use of SEFA method and caudalizing factor can induce differentiation into cells corresponding to caudal tissue.

Example 7

Changes in Subregional Markers by Patterning Factor

Then, we tried to examine whether or not the expression of subregional markers in SFEB is varied by exogenous patterning factors. Moreover, Shh (manufactured by R&D) was used as the patterning factor.

As a result, addition of 3-300 nM Shh to medium on or after fourth days of the culture by SFEB method significantly decreased the percentage of Pax6$^+$ cells among Bf1$^+$ cells in a dose-dependent manner, and increased the percentage of ventral cells such as NRx2.1$^+$ cells and Gsh$^+$ cells about two times. The percentage of Bf1$^+$ cells in total cells was not affected by Shh treatment. Furthermore, Shh treatment increased neurons of ventral telencephalon characters (Bf1$^+$/Islet1/2$^+$, ChAT$^+$) in long period culture of SFEB-induced neural tissue, while it suppressed differentiation into GluT1$^+$ glutamatergic-producing neurons (typically dorsal), indicating that telencephalic neurons induced by SFEB respond to Shh signaling in a similar fashion to those in the embryo.

From the above, combination of SFEB method with Shh treatment can efficiently induce differentiation into ventral telencephalic neurons, and the telencephalic neurons induced by SFEB method respond to Shh signaling in a similar fashion to those in the embryo.

Example 8

Induction of Differentiation into Dorsal Telencephalic tissue by Wnt Signal Factor ES cells were cultured by the SFEB method in the same manner as Examples 4 and 6 for 5 days to induce neural differentiation, subsequently dispersed by trypsin/EDTA treatment, seeded to a cell culture slide coated with poly-D lysine/laminin, and cultured. Wnt3a was added at a concentration of 5 ng/ml or 50 ng/ml, starting on Day 6, and the cells were cultured for a total of 10 days; the number of cells positive for both NRx2.1 and Bfl, which are ventral telencephalon markers, decreased remarkably, whereas the number of cells positive for both Pax6 and Bfl, which are dorsal telencephalon markers, increased. In the case of 50 ng/ml Wnt3a, about 75% of the Bf1-positive cells expressed the dorsal marker Pax6, and about 10 percent of them expressed Emx1, a marker of cerebrocortical precursor cells.

Hence, it was suggested that by allowing a Wnt signal to act in the late stage of cultivation in the SFEB method, dorsal telencephalic cells could be differentiation-induced efficiently.

Example 9

Induction of Differentiation into Cerebellar Nerve Precursor Cells with a Combination of BMP and Wnt ES cells were subjected to neural differentiation-induction by the SFEB method in the same manner as Example 4 except that serum-free floating culture was continued for 7 days. During the 1 day of cultivation from Day 7 of cultivation, floating culture using a Neurobasal (manufactured by Gibco)

medium supplemented with B27 supplement (manufactured by Gibco) was continued. From 5 days later to Day 8 of cultivation, 0.5 nM BMP4 (manufactured by R&D), 10 ng/ml Wnt3a (manufactured by R&D), and 50 ng/ml FGF8b (manufactured by R&D) were added to the medium. Eight days after the start of cultivation, cell clamps, as is or after dispersion by trypsin/EDTA treatment, were seeded to a cell culture slide coated with poly-D lysine/laminin, and adhesion culture was performed using a Neurobasal medium supplemented with B27 supplement. Immunostaining was performed on Day 9; a large number of cells expressing Math1, Pax6, or Zic1, which are markers specific for precursor cells of cerebellar granule cells, were observed. 40 to 50% of the cells were positive for Math1, of which not less than 50% were positive for Pax6 or Zic1. Furthermore, it is known that precursor cells of cerebellar granule cells include vigorously dividing cells, and about half of the Math1-positive cells had expressed Ki67, a marker specific for cells capable of division. Although treatment with BMP and Wnt was essential to this induction of granule cell markers, treatment with FGF was not essential.

Furthermore, adhesion culture was started while the cells were in the form of cell clamps on Day 8 of cultivation, and the cells were cultured for a total of 20 days; it was confirmed that a plurality of (about 10) large neurons positive for L7, a cerebellar Purkinje's cell-specific marker, were present in about 50% of the cell clamps. This differentiation induction efficiency was achieved with a combination of BMP4 and Wnt; an examination of a combination with FGF8b showed that a combination of BMP4 and FGF8b was also effective for the differentiation of cerebellar Purkinje's cells, unlike for the differentiation into granule cells, and the number of positive cells increased 4 fold compared to the combination of BMP4 and Wnt.

To separate precursor cells for cerebellar granule cells, a cell line was established by transfecting EB5 cells with a marker gene having GFP joined downstream of the Math1 promoter (Development 127, 127, 1185-1196 (2000)) by an ordinary method. A GFP-positive fraction was separated from cells cultured for 8-10 days as directed above, using a fluorescence cell sorter; about 90 percent of the cells were purified into cells positive for Math1-GFP. These cells had expressed Pax6, Zic1 and the like. Also, by allowing these cells to aggregate with dispersed cells of mouse fetal cerebellum or neonatal cerebellum, and co-culturing them, differentiation into neurons was induced (Development 106, 441-447 (1989); Development 128, 3133-3144 (2001)). Thus, the cells differentiation-induced from ES cells were observed to move in adhesion to parallel fiber axons elongated by mouse cerebellum-derived cerebellum cells on Day 2 (a characteristic of cerebellar granule cells), and were further confirmed to have elongated T-shaped axons per se, a characteristic of cerebellar granule cells, on Days 2-3 after the start of co-cultivation.

Hence, it was suggested that neurons of cerebellar tissue can be differentiation-induced by using the method of the present invention in combination with BMP and Wnt.

Example 10

Induction of Differentiation into Cerebellar Nerve Precursor Cells with a Combination of BMP and Wnt Although there have been no reports on differentiation induction of ES cells into cerebellar tissue, the present inventors have already reported that Math1 is induced by treating neurons differentiated by the SDIA method with BMP4 (see Proc. Natl. Acad. Sci. USA, 100, 5828-5833). However, in addition to the cerebellum, Math1 is expressed in the neurons of dorsal central nervous organs such as the pons, medulla oblongata, and spinal cord; the expression of Math1 alone does not suffice to judge the generated tissue to be cerebellar tissue. Hence, ES cells were seeded onto PA6 cells and cultured for 9 days by the SDIA method, with 0.5-1 nM BMP4 added starting on Day 4 or Day 5; about 10 to 20 percent of the cells became positive for Math1. However, most of these cells did not express Pax6, Zic1 and the like, which are other cerebellar granule cell markers, and were negative for Ki67 (a marker for cells capable of division). Therefore, the Math1-positive cells induced by the SDIA method were postulated not to be cerebellar granule cells, but to be Math1-positive cells of the pons, medulla oblongata, spinal cord and the like.

Hence, it was confirmed that the present inventors succeeded for the first time in differentiation-inducing cerebellar neurons from ES cells by the method of the present invention.

Example 11

Induction of Differentiation into Retinal Precursor Cells by the SFEB Method

EB5 cells were subjected to serum-free floating culture by the SFEB method for 5 days, after which cell clamps as is were seeded to a cell culture slide coated with poly-D lysine/laminin/fibronectin, and cultured while in the KSR-containing differentiation medium for the SFEB method for a total of 8 days. Immunostaining was performed using an internally prepared antibody against Rx, a marker specific for retinal precursor cells; an Rx-positive cell population was identified in about 15-30% of the cell clamps (colonies). By treatment with 5% fetal calf serum or 100 ng/ml activin (manufactured by R&D) or treatment with 3-30 nM Shh during 3 to 5 days after the start of cultivation, the Rx positivity rate of colonies increased to 50% (about 2 times). Furthermore, by separately adding 1 µg/ml Dkk1 and 0.5 µg/ml Lefty-A on Days 0-5 of cultivation, about 70 percent of the colonies became positive for Rx, and even at the cellular level, about 10-15% of the cells became positive. It is also possible to further perform treatment with serum, Shh, or activin simultaneously with Dkk1 and Nodal treatment; the colony positivity rate further rose by about 5-10%. Also, these cells were subjected to adhesion culture for a long time (a total of 14 to 18 days); a plurality of cells positive for the visual cell marker Crx or rhodopsin were identified in 1-5% of the colonies. When ES cells were cultured by the SFEB method in the presence of Lefty A (added on Days 0-5), Dkk1 (added on Days 0-5), serum (added on Days 3-5 only), and activin (added on Days 4-6 only), 20-30 percent of all the cells differentiated into retinal precursor cells; after these cells were fluorescently labeled, they were co-cultured for 12 days with mouse retinal tissue at E17.5 days, and 20 percent of the cells became positive for the visual cell marker rhodopsin. Particularly, for the cells entering the visual cell layer of retinal tissue, 40 percent of them were positive for the marker rhodopsin and exhibited morphologies specific for visual cells, such as outer segment structure.

Example 12

Neural Differentiation Induction Using Human ES Cells

Human ES cells, specifically human blastocyst-derived embryonic stem cells established at Norio Nakatsuji's laboratory in the Institute for Frontier Medical Sciences, Kyoto University, were kindly provided in accordance with the Guidelines for Human ES Cells, and subjected to maintenance culture on a plastic culture dish seeded with mouse fetal fibroblasts (inactivated by mitomycin treatment; MEF) at 37° C. under 5% $CO_2$ in accordance with the method of Norio Nakatsuji's laboratory. The culture medium used was prepared by adding to the base D-MEM-F12 (Sigma D6421) a final concentration of 20% of KSR (invitrogen/Gibco-BRL), 1×NEAA (non-essential amino acids; invitrogen/Gibco-BRL), 2 mM L-glutamic acid, and 0.1 mM 2-mercaptoethanol. Subculture was performed every 3-4 days; ES cells were dissociated from the feeder cells using a dissociation solution (phosphate-buffered physiological saline supplemented with 0.25% trypsin, 1 mg/ml collagenase IV solution, and 1 mM $CaCl_2$; all from invitrogen/Gibco-BRL), and prepared as about 100 small clamps by pipette operation, after which they were seeded over the feeder layer of MEF seeded on the previous day.

For neural differentiation induction, the above-described small clamps of dissociated ES cells were seeded to 35 mm culture dishes at a ratio of 3500 clamps per dish, and serum-free floating aggregate culture was performed for 15 days. The culture medium used was 2 ml of differentiation induction medium (medium supplemented with G-MEM, KSR, and 2-mercaptoethanol in the same manner as used in mouse ES cells, but KSR was added at 5%, 10% or 20%). Furthermore, during the first 10 days after the start of differentiation induction culture, the Nodal inhibitor Lefty A (1 μg/ml), the Wnt inhibitor Dkk1 (500 ng/ml), and the BMP inhibitor soluble BMPR1A-Fc (1.5 μg/ml; all manufactured by R&D Company) were added. After 15 days of serum-free floating culture, the cells were seeded onto culture dishes coated with poly-D-lysine/laminin/fibronectin, adhesion culture (the culture medium was the same differentiation induction medium) was performed for 5 days, and fixation and immunostaining were performed.

As a result, the human ES cells permitted serum-free floating aggregate culture in the presence of KSR at 10% and 20%. With 5% KSR, their proliferation was poor, and many died during 15 days of floating culture. In immunostaining after 5 days of adhesion culture, nearly all cell colonies were positive for the nerve precursor cell marker nestin, and negative for the undifferentiated ES cell marker Oct3/4. For the cerebral precursor cell marker Bf1, 50% of the colonies were positive.
(Discussion)
Selective Neural Differentiation in SFEB We have succeeded development of methods of culturing floating aggregate, which enables selective neural differentiation of ES cells in vitro. The efficiency, speed and simplicity of the procedure are comparable to those of the SDIA method. The SFEB method does not require the presence of feeder cells, serum or growth factors with neural patterning activities (e.g. FGF, BMP, Wnt). Instead, the efficiency of neural differentiation is even more enhanced when endogenous Wnt and Nodal signal are antagonized. These observations indicate that floating aggregates of ES cells autonomously initiate neural differentiation program in the absence of inhibitory factors. In contrast to embryoid body (EB) cultured in serum-containing medium, which efficiently produce the primitive endoderm and mesoderm, less than 4% SFEB aggregates contain only a small portion of cells which are positive for primitive endodermal marker AFP and Hnf4 or the mesodermal marker Branchyury.

Interestingly, floating culture of ES cell aggregates itself seems to have different effects on cell fate specification from adhesion culture. For example, BMP treatment (5 nM) of ES cells cultured on collagen-coated dish induces efficient differentiation into flk1$^+$ lateral plate mesoderm. In contrast, BMP treatment of ES cells cultured on SFEB method efficiently produces E-cad$^+$/Oct3/4$^-$ cells (typically non-ectoderm), but not flk1$^+$ cells while it completely suppresses neural differentiation. It is interesting to elucidate what kinds of signaling regulate this difference by analyzing RNA profile for them.

INDUSTRIAL APPLICABILITY

According to the method of the present invention, because nervous system cells and sensory organ cells can be differentiation-induced efficiently, it enables the application of cell therapy for neurodegenerative disease, sensory organ disease and the like. Also, according to the method of the present invention, because forebrain tissue (particularly telencephalic tissue), which has been difficult to differentiate by conventional differentiation methods, can be differentiation-induced efficiently, and also because it enables the induction of differentiation into cerebellar tissue, which has conventionally been impossible, it enables the application of cell therapy for diseases characterized by abnormalities in forebrain tissue or cerebellar tissue. Furthermore, according to the present invention, because no animal-derived cell is used as the induction source, the risk of transplantation of cells obtained by culturing embryonic stem cells can be lessened to the risk level of allograft.

This application is based on a patent application No. 2004-181770 filed in Japan on Jun. 18, 2004, the contents of which are incorporated herein by reference.

The invention claimed is:

1. A method of inducing differentiation of mammalian embryonic stem cells into retinal system cells, which method comprises
    (a) producing a floating aggregate of embryonic stem cells in a serum-free medium in the absence of feeder cells, and
    (b) culturing the floating aggregate in a serum-free medium comprising a Nodal signal inhibitor and a Wnt signal inhibitor in the absence of feeder cells,
    thereby inducing differentiation of the embryonic stem cells into retinal system cells.

2. The method of claim 1, wherein the Nodal signal inhibitor is Lefty-A.

3. The method of claim 1, wherein the Wnt signal inhibitor is Dkk1.

4. The method of claim 1, wherein the concentration of the embryonic stem cells at the start of cultivation is $1 \times 10^4$ to $5 \times 10^5$ cells/ml.

5. The method of claim 1, wherein cultivation of the embryonic stem cells is performed in a non-cell-adhesive culture vessel.

6. The method of claim 1, which comprises culturing the floating aggregate of the embryonic stem cells for at least 5 days.

7. The method of claim 1, which further comprises culturing cells obtained in step (b) under adherent conditions.

8. The method of claim 1, which further comprises adding an Shh signal promoter to the serum-free medium comprising the floating aggregate.

9. The method of claim 8, wherein the Shh signal promoter is Shh.

10. The method of claim 8, wherein the Shh signal promoter is added to the serum-free medium within 3 to 7 days after the start of the culture of the floating aggregate.

11. The method of claim 1, which further comprises adding serum to the serum-free medium comprising the floating aggregate.

12. The method of claim 11, wherein the serum is added to the serum-free medium within 3 to 7 days after the start of the culture of the floating aggregate.

13. The method of claim 1, which further comprises adding activin to the serum-free medium comprising the floating aggregate.

14. The method of claim 13, wherein the activin is added to the serum-free medium within 3 to 7 days after the start of the culture of the floating aggregate.

15. The method of claim 11, wherein the floating aggregate of the embryonic stem cells is cultured in the presence of Lefty-A, Dkk1, and activin.

16. The method of claim 1, wherein the retinal system cells are retinal precursor cells.

17. The method of claim 1, wherein the serum-free medium is (i) a medium substantially not comprising one or more items selected from the group consisting of FGF, RA, and a BMP signal promoter, or (ii) a medium wherein one or more items selected from the group consisting of FGF, RA and a BMP signal promoter, have been substantially inactivated.

18. The method of claim 1, wherein the serum-free medium is a medium substantially not comprising a Nodal signal promoter and/or a Wnt signal promoter.

* * * * *